United States Patent [19]

Jakubke et al.

[11] Patent Number: 5,350,682
[45] Date of Patent: Sep. 27, 1994

[54] PROCESS FOR PREPARING PEPTIDES

[75] Inventors: Hans-Dieter Jakubke, Leipzig; Matthias Schuster, Berlin; Aavo Aaviksaar, Tallinn, all of Fed. Rep. of Germany

[73] Assignee: Hoechst Aktiengesellschaft, Frankfurt am Main, Fed. Rep. of Germany

[21] Appl. No.: 956,025

[22] PCT Filed: May 10, 1991

[86] PCT No.: PCT/EP91/00877

§ 371 Date: Feb. 12, 1993

§ 102(e) Date: Feb. 12, 1993

[87] PCT Pub. No.: WO91/19811

PCT Pub. Date: Dec. 26, 1991

[30] Foreign Application Priority Data

Jun. 13, 1990 [DE] Fed. Rep. of Germany ....... 3416031

[51] Int. Cl.$^5$ ............... C12P 21/00; C12N 9/76; C12N 9/50
[52] U.S. Cl. .................. 435/68.1; 435/213; 435/219
[58] Field of Search .............. 435/68.1, 213, 219

[56] References Cited

U.S. PATENT DOCUMENTS 4,256,836  3/1981  Isowa et al. ................. 435/70
4,935,355  6/1990  Ulmer ...................... 435/68.1

OTHER PUBLICATIONS

"Grundprinzipien der proteasekatalysierten Knupfung der Peptidbindung", Jakubke, Kuhl und Konnecke, Angewandte Chemie, 97 (1985) 79–87.

"Basic Principles of Protease-Catalyzed Peptide Bond Formation", Jakubke et al., Angew. Chem. Int. Ed. Engl. 24 (1985), No. 2, pp. 85–93.

"Proteinase-Catalyzed Synthesis of Peptide Bonds", Fruton, A. Meister Adv. Enzymmol. Relat. Areas Mol. Biol., 53, (1982), pp. 239–306.

"Proteasen als Biokatalysatoren fur die Peptidsynthese", Jakubke et al., Die Pharmazie 37, (Feb. 1982), pp. 89–106.

"Protease-catalyzed peptide synthesis: effect of temperature on the kinetics of acyl transfer catalyzed by papain", Gololobov et al., Chemical Abstracts, abstract No. 232227p, 112(25):314 (1990).

"Enzyme-catalyzed Peptide Synthesis In Ice", Schuster et al., Tetrahedron, 46(24): 8093–8102 (1990).

*Primary Examiner*—Herbert J. Lilling
*Attorney, Agent, or Firm*—Finnegan, Henderson, Farabow, Garrett & Dunner

[57] ABSTRACT

The invention relates to a process for preparing chirally uniform peptides. The aim of the invention is the preparation of chirally uniform peptides with the aid of proteolytic enzymes. The object comprises reacting alkyl esters of N-acylamino acids with proteases with amino acids, amino acid derivatives or peptides. The object is achieved by reacting an ester of an N-acylamino acid with a suitable amino acid derivative or peptide derivative with an unprotected N-terminal alphaamino group in frozen aqueous solution during catalysis with a serine protease or cysteine protease.

4 Claims, No Drawings

PROCESS FOR PREPARING PEPTIDES

AREA OF APPLICATION OF THE INVENTION

The invention relates to a process for preparing peptides which, after the splitting off of protective groups, can serve as active substances or intermediates of active substances.

DESCRIPTION OF THE KNOWN STATE OF THE ART

Various organic chemical processes can be employed for the preparation of peptides (cf. Review: Wünsch, E. (1974) Synthesis of Peptides, in Houben-Weyl, Vol. 15, ½, Methoden der organischen Chemie (Methods of organic chemistry), Müller, E. (Ed.) Georg Thieme Verlag, Stuttgart). During the course of chemical peptide syntheses, undesirable side reactions are frequently observed which decrease the yield and render necessary difficult and lengthy purification procedures. A particularly serious disadvantage of the conventional processes is the unsolved problem of racemization which appears in particular in relation to segment condensation using chemical coupling methods. Since it is very difficult to separate stereoisomers from each other completely, and the optical purity of the products of synthesis is a necessary prerequisite for biological activity, the industrial synthesis of peptides by means of organic chemical processes has substantial disadvantages. Furthermore, because of the danger of side reactions, the third functionalities of amino acid building blocks must be reversibly blocked in all chemical operations for synthesizing peptides. The use of biocatalysts for the catalysis of the peptide coupling step offers a means of circumventing the difficulties described (cf. Reviews: Jakubke, H.-D., and Kuhl, P. (1982) Pharmazie 37 89; Fruton, J. S. (1982) in A. Meister: Adv. Enzymmol. Relat. Areas Mol. Biol. 53, 239; Jakubke, H.-D., Kuhl, P. and Könnecke, A. (1985) Angew. Chem. 97, 79). As a result of the stereospecificity of the proteases employed as biocatalyst, chiral integrity is preserved and the high degree of reaction control makes it possible, to a large extent, to dispense with protection of third functionalities. Kinetic control of the reaction plays a key role within the framework of enzyme-catalyzed peptide synthesis. The hydrolysis of the acyl-enzyme intermediate that is involved with peptide product formation in this method still represents a problem for many synthesis reactions, since the yield of peptide product remains limited.

AIM OF THE INVENTION

The aim of the invention is to prepare chirally uniform peptides with greatly reduced hydrolysis of the acyl-enzyme intermediate as compared with previously employed methods.

EXPLANATION OF THE NATURE OF THE INVENTION

The basic object of the invention is to react alkyl esters of N-acylamino acids in the presence of proteases with amino acids, amino acid derivatives or peptides with an unprotected N-terminal alpha-amino group as the amino component.

According to the invention, peptides are prepared from an amino acid with a protected alpha-amino group or a peptide with a protected alpha-amino group, whose carboxyl group entering into the reaction is present as an ester, and from an amino acid, an amino acid derivative or a peptide, in which the amino group entering into the reaction is unblocked, in the presence of a protease in frozen aqueous solution, which optionally contains organic solvent constituents and/or buffer substances. Peptides are formed in high yields and can be preparatively separated by suitable chromatographic or extractive techniques. In contrast to known syntheses of peptides using proteases, a far higher yield of peptide is obtained by the freezing of the reaction mixture according to the invention. In one embodiment the enzyme-catalyzed reactions are carried out in a temperature range from $-1°$ C. to $-40°$ C.

This is the first time that the enzyme-catalyzed synthesis of the peptide class of compounds has been described in frozen aqueous systems. The effect of the invention is surprising inasmuchas a decrease in yield, which is essentially caused by the formation of by-products, is generally associated with a lowering of temperature and the consequent deceleration of the reaction velocity. Unexpectedly, a high yield is obtained of preferably one, the desired, product.

TABLE 1

Comparison of the yield of protease-catalyzed peptide synthesis reactions in aqueous liquid phase (25° C.) and in frozen aqueous phase ($-25°$ C.)
(carboxyl component) = 2 mM, (amino component) = 50 mM

| Carboxyl comp. | Amino comp. | Enzyme | Peptide yield (%) 25° C. | Peptide yield (%) $-25°$ C. |
|---|---|---|---|---|
| Mal—Phe—Ala—OEtCl | H—Ala—Ala—OH | Papain | 42 | 79 |
| Z—Glu—OMe | H—Ala—Ala—OH | Endoprot.Glu—C | 5 | 76 |
| Mal—Tyr—OMe | H—Ala—Ala—OH | α-Chymotrypsin | 10 | 94 |
| Mal—Tyr—OMe | H—D—Leu—NH$_2$ | α-Chymotrypsin | 10 | 73 |
| Mal—Tyr—OMe | H—Lys—OH | α-Chymotrypsin | 2 | 44 |
| Mal—Tyr—OMe | H—β—Ala—Gly—OH | α-Chymotrypsin | 13 | 79 |

EMBODIMENT EXAMPLES

In the examples the amino acids are abbreviated according to the internationally valid rules. Additionally the following abbreviations are used:
Z benzyloxycarbonyl
Mal maleyl
OMe methyl ester
OEtCl monochloroethyl ester Unless otherwise indicated, amino acids and amino acid residues with an optically active center have the L configuration.

EXAMPLE 1

Synthesis of Mal-Phe-Ala-Ala-Ala-OH 0.2 ml of aqueous solution containing 2 mM Mal-Phe-Ala OEtCl, 50 mM H-Ala-Ala-OH, 25 mM NaOH and 0.15 mg/ml papain are deep-frozen. Subsequently the reaction mixture is kept at −25° C. until the Mal-Phe-Ala-OEtCl is consumed. Following thawing, the yield is determined analytically by RP-HPLC and amounts to 79% of theory.

EXAMPLE 2

Synthesis of Z-Glu-Ala-Ala-OH 0.2 ml of aqueous solution containing 2 mM Z-Glu-OMe, 50 mMH-Ala-Ala-OH, 25 mMNaOH and 5 mg/ml endoproteinase Glu-C are deep-frozen. Subsequently the reaction mixture is kept at −25° C. until the Z-Glu-OMe is consumed. Following thawing, the yield is determined analytically by RP-HPLC and amounts to 76% of theory.

EXAMPLE 3

Synthesis of Mal-Tyr-Ala-Ala-OH 0.2 ml of aqueous solution containing 2 mM Mal-Tyr-OMe, 50 mM H-Ala-Ala-OH, 25 mM NaOH and 0.3 M α-chymotrypsin are deep-frozen. Subsequently the reaction mixture is kept at −25° C. until the Mal-Tyr-OMe is consumed. Following thawing, the yield is determined analytically by RP-HPLC and amounts to 94% of theory.

EXAMPLE 4

Synthesis of Mal-Tyr-D-Leu-NH

As in Example 3, but with 50 mM H-D-Leu-$NH_2$ as the amino component. Yield, 73% of theory.

EXAMPLE 5

Synthesis of Mal-Tyr-Lys-OH

As in Example 3, but with 50 mM H-Lys-OH as the amino component. Yield, 44% of theory.

EXAMPLE 6

Synthesis of Mal-Tyr-β-Ala-Gly-OH

As in Example 3, but with 50 mM H-β-Ala-Gly-OH as the amino component. Yield, 79% of theory.

What is claimed is:

1. A process for preparing peptides from amino acids or corresponding peptides, which are blocked with an alpha-amino protective group and whose carbonyl function entering into the reaction carries an ester group, by reaction with amino acids, amino acid derivatives or peptides with an unprotected alpha-amino function, wherein the reaction is carried out, using catalysis by an enzyme selected from the group consisting of serine proteases and cysteine proteases in aqueous solution in a temperature range from −1° C. to −40° C., which aqueous solution optionally contains organic solvent constituents and/or buffer substances, and after completed coupling and working up the protective groups are partially or completely removed.

2. The process as claimed in claim 1, wherein, instead of buffer substances, the buffering capacity of the unprotected amino group entering into the reaction is used.

3. The process as claimed in claims 1 or 2, wherein enzyme is bound to a carrier.

4. The process as claimed in claim 1 wherein the enzyme is α-chymotrypsin, endoproteinase Glu-C, or papain.

* * * * *